United States Patent
Patel et al.

(10) Patent No.: US 7,220,713 B2
(45) Date of Patent: May 22, 2007

(54) LOW AMOUNTS OF HIGH MOLECULAR WEIGHT POLYMERS FOR ENHANCING VISCOSITY OF AQUEOUS/AQUEOUS BIPHASIC LIQUIDS

(75) Inventors: Rajesh Patel, Middlebury, CT (US); Rosa Paredes, Shelton, CT (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 269 days.

(21) Appl. No.: 11/104,934

(22) Filed: Apr. 13, 2005

(65) Prior Publication Data

US 2006/0234897 A1    Oct. 19, 2006

(51) Int. Cl.
*C11D 1/00* (2006.01)
*C11D 3/22* (2006.01)
*C11D 3/37* (2006.01)

(52) U.S. Cl. ............. 510/130; 510/159; 510/405; 510/417; 510/421; 510/426; 510/470; 510/474; 510/475; 510/483; 510/535

(58) Field of Classification Search ......... 510/130, 510/159, 405, 417, 421, 426, 470, 474, 475, 510/483, 535
See application file for complete search history.

(56) References Cited

U.S. PATENT DOCUMENTS

| | | |
|---|---|---|
| 3,718,609 A | 2/1973 | Weimer |
| 3,810,478 A | 5/1974 | Olson, Jr. et al. |
| 6,180,587 B1 | 1/2001 | Fuller et al. |
| 6,429,177 B1 | 8/2002 | Williams et al. |
| 6,727,209 B2 | 4/2004 | Pereira et al. |
| 6,787,511 B2 | 9/2004 | Patel et al. |
| 2004/0033914 A1* | 2/2004 | Patel et al. ......... 510/130 |

FOREIGN PATENT DOCUMENTS

EP    0 116 422    8/1984

* cited by examiner

*Primary Examiner*—Brian Mruk
(74) *Attorney, Agent, or Firm*—Ronald A. Koatz

(57) ABSTRACT

The invention provides high molecular weight polymers used in small amounts as viscosity modifiers for aqueous/aqueous biphasic liquids. The viscosity of the biphasic is enhanced at least 20%, preferably at least 30% relative to same compositions without use of polymer. Further, the polymer is included without destroying the ability of dual phase compositions to form after product is left standing.

15 Claims, No Drawings

LOW AMOUNTS OF HIGH MOLECULAR WEIGHT POLYMERS FOR ENHANCING VISCOSITY OF AQUEOUS/AQUEOUS BIPHASIC LIQUIDS

FIELD OF THE INVENTION

The present invention relates to aqueous liquid compositions that are biphasic in nature. In particular, it relates to use of high molecular weight polymers in such compositions to enhance the viscosity of the compositions when in a single phase and without destroying the ability to induce good phase separation in such compositions.

BACKGROUND

Biphasic liquids defined by the general fact that the liquid is divided into two phases are not new. In some of these liquids, one layer is an aqueous layer and the second layer is a water inmmiscible oily material, while in others both layers are aqueous based.

U.S. Pat. No. 3,718,609 issued to Weimer on Feb. 27, 1973 discloses a liquid detergent composition having an aqueous layer and a layer of liquid water immiscible oily material. When shaken, the liquid forms a temporary oil-in-water emulsion.

Similarly, U.S. Pat. No. 3,810,478, issued to Olson Jr. et al. on May 14, 1974, discloses a two-phase shampoo composition made by preparing substantially polar and lipophilic portions of a shampoo composition.

Biphasic compositions comprising an upper and lower aqueous phase are also disclosed in the art. U.S. Pat. No. 6,429,177 issued to Williams et al. on Aug. 6, 2002 discloses biphasic compositions including 5 to 35% surfactant; 1 to 12% thickener; 4 to 20% polyalkylene glycol; and a sufficient amount of non-chelating mineral salt to induce phase separation.

U.S. Pat. No. 6,180,587 issued to Fuller et al. on Jan. 30, 2001 disclose multiphase cleansing compositions having at least 1% of a polymer or copolymer selected from the group consisting of polyacrylate, polystyrene sulfonate, polyvinylpyrrolidone, maleic anhydride and their mixtures.

EP 0,116,422 to Harmer published on Apr. 6, 1988 also discloses multi-layered compositions in which two liquids are dispersible and which separate on standing. Sodium hexamataphosphate is a preferred biphasic inducing agent required in these compositions.

In U.S. Pat. No. 6,787,511 issued to Patel et al. on Sep. 7, 2004, and U.S. Pat. No. 6,727,209 issued to Pereira et al. on Apr. 27, 2004, the current inventors reported that polydextrose of molecular weight between about 600 and about 3,000 Daltons, used alone or in combination with a salt such as $MgSO_4$ and/or sucrose, induced biphasic liquid formation. While these compositions are adequate, they do not have a particularly high viscosity, particularly the type of viscosity suitable for liquid cleansers targeted to personal cleansing (e.g., shower gels and shampoos). One of the goals of the subject invention was to provide small amounts (e.g., under 1% by wt.) of high molecular weight polymers which could raise the viscosity to levels more suitable for such shower gels and/or shampoos.

In a co-pending application filed on Dec. 28, 2004 to Patel et al., applicants disclose specific biphasic inducing agents (BIA) that can be used alone or in combination with polydextrose and/or salt. Two classes of the new BIA are specific polysaccharides that surprisingly have much higher molecular weights than the optimal polydextrose oligomers described in U.S. Pat. Nos. 6,787,511 and 6,727,209 noted above; and intermediate ethoxylates of fatty esters or fatty acids. These BIAs can be used alone and are used for purpose of economy or to provide opacity. The high MW polymers of the subject invention, by contrast, are always used as adjunct materials (i.e., less than 1% by wt.) and are specifically used to enhance viscosity of previously known biphasic compositions (for example as taught in U.S. Pat. No. 6,787,511 or U.S. Pat. No. 6,727,209). Moreover, they enhance viscosity while retaining ability to induce phase separation in the compositions.

As noted, the present invention relates to use of low amounts of high molecular weight polymers (e.g., thickeners of at least certain MW, wherein some class of viscosity building polymers are particularly preferred) to further enhance the viscosity of aqueous/aqueous biphasic liquids after they have been stirred/agitated and are in one phase. The amounts cannot be too high without destroying ability to adequately phase separate.

BRIEF DESCRIPTION OF THE INVENTION

Unexpectedly, applicants have now found novel biphasic compositions comprising small amounts (0.01 to 1% by wt.) of high MW viscosity building polymers, and process for enhancing viscosity of biphasic liquids (particularly those induced by polydextrose) using low amounts of such high molecular weight polymers.

In one embodiment, the invention comprises:
(a) 5 to 70%, preferably 5 to 50% by wt. of a surfactant selected from the group consisting of anionic surfactants, nonionic surfactants, amphoteric/zwitterionic surfactants, cationic surfactants and mixtures thereof;
(b) 1 to 12% by wt. thickener;
(c) 4 to 20% by wt. polyalkylene glycol;
(d) a non-chelating mineral salt selected from alkali metal or alkaline earth sulfates, bisulfates, carbonates, bicarbonates, and mixtures thereof,
  wherein the non-chelating mineral salt is present in an amount sufficient to induce a separation of the aqueous composition into at least two distinct aqueous layers that are present in a volume ratio of upper to lower phase of from 4:1 to 1:4;
  wherein on standing the personal product composition forms two or more visibly distinct aqueous phases and, when agitated, the composition forms a visible single phase product,
  wherein, when left to stand after the composition has been agitated and has formed a single phase, the composition will again form two or more visibly distinct aqueous phases within 24 hours; and
(e) 0.01 to less than 1% by wt. of viscosity building polymer and/or copolymer having molecular weight of at least 5,000, preferably at least 10,000, more preferably at least 25,000 (no upper limit although, as a practical matter, limit is 500,000 preferably 300,000, more preferably 200,000),
  wherein said polymer enhances viscosity (of the single phase solution, after agitation) at least 5%, preferably at least 10%, preferably at least 20%, more preferably at least 30% relative to same composition without polymer.

As a practical matter, there is a balance between molecular wt. and how much polymer is added. As the molecular weight of polymer increases, less amount is needed. While not wishing to be bound by theory, this is believed due to requirement to maintain phase separation.

In a preferred embodiment, the composition comprises:
(a) 5 to 70%, preferably 5 to 50% of a surfactant selected from the group consisting of anionic surfactants, nonionic surfactants, amphoteric/zwitterionic surfactants, cationic surfactants and mixtures thereof;
(b) at least about 15% of a polydextrose molecule or molecules, wherein the degree of polymeric cation is about 4 to 22 (corresponding to MW about 600 to about 3600);
(c) balance water and minors,
 wherein said composition comprises at least two visibly separated aqueous based layers when left sitting without shaking or stirring; and
(d) 0.01 to less than 1% by wt. of viscosity building polymer and/or copolymer having molecular weight of at least 5,000, preferably at least 10,000, more preferably at least 25,000,
 wherein said polymer enhances viscosity at least about 20%, preferably at least 30% relative to same composition without polymer.

The same practical limitations to the upper molecular weight and regarding the balance of molecular wt. to the amounts used apply as noted above for first embodiment.

In a third embodiment of the invention, the invention comprises a method of enhancing viscosity of aqueous/aqueous biphasic liquids when they are in a single phase after agitation, which method comprises using, in the process for preparing said compositions, 0.01 to less than 1% of a polymer and/or copolymer having a MW of at least 5,000, preferably at least 10,000, preferably at least 25,000. The polymers which may be used are discussed in more detail below.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental examples, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y", it is understood that all ranges combining the different endpoints are also contemplated. Where the term "comprising" is used in the specification or claims, it is not intended to exclude any terms, steps or features not specifically recited. All temperatures are in degrees Celsius (° C.) unless specified otherwise. All measurements are in SI units unless specified otherwise. All documents cited are—in relevant part—incorporated herein by reference.

DETAILED DESCRIPTION OF THE INVENTION

The subject invention relates to the use of low amounts of high molecular weight polymers uses to unexpectedly enhance viscosity of aqueous/aqueous biphasic liquids (especially those induced using polydextrose). The invention further relates to biphasic compositions comprising low amounts of such polymers. Use of amounts too high may affect ability of compositions to phase separate after agitation.

Specifically, these high molecular weight polymers are used to enhance viscosity of typical aqueous/aqueous biphasic liquids known in the art in order to obtain viscosity levels more suitable for, for example, shampoos, body liquids etc. for which the compositions are often intended.

In this regard, in one embodiment the invention relates to aqueous/aqueous biphasic liquid compositions formed using polyalkylene glycol and defined salts as biphasic inducing agent (such compositions typically include some thickeners). Typically, such compositions are described in U.S. Pat. No. 6,429,177 to Williams et al., for example. In this embodiment, the high molecular weight copolymers of the invention are also present and serve to enhance viscosity relative to same composition without the high molecular weight polymer (e.g., enhance viscosity at least 5%, preferably at least 10%, more preferably at least 20%, more preferably 20% to 100% or more relative to same composition without polymer).

In a second, preferred embodiment, the invention relates to aqueous/aqueous biphasic liquid compositions formed using defined polydextran molecule or molecules as biphasic inducing agent. Typical such compositions are described, for example, in U.S. Pat. No. 6,787,511 to Patel et al. Again, the high MW polymer of the invention serves to remarkably enhance viscosity relative to same compositions without the polymer (e.g., 5% to 100% or more preferably at least 10%, more preferably at least 20%, more preferably at least 30% relative to same composition without polymer).

In a third embodiment, the invention relates to process for enhancing viscosity of aqueous/aqueous biphasic liquid compositions at least 5, preferably at least 10%, more preferably at least 20% to 100% by ensuring that the compositions, when formed, incorporate the defined high molecular weight polymers of the invention.

As noted, in one embodiment, the invention relates to aqueous/aqueous biphasic compositions formed using polyalkylene glycol and defined salts as biphasic inducing agent.

Typically, such compositions are, prior to mixing, found in two phases (upper and lower aqueous phases) comprising:
(1) an upper aqueous layer comprising:
 (a) 5–35% by wt. of total composition (10 to about 75% by wt. upper aqueous phase in part depending on ratio of upper layer to lower layer) of a lathering surfactant selected from the group consisting of anionic surfactants, nonionic surfactants, amphoteric/zwitterionic surfactants, cationic surfactants and mixtures thereof (preferably at least one anionic should be present);
 (b) 4% to 25% by wt. of total composition, preferably 7 to 20% by wt. of a polyalkylene glycol selected from the group consisting of alcohols or polyethers having MW 200 to about 6000;
 (c) 1–12% by wt. of total composition, preferably 2 to 10% by wt. of a thickener/viscosity modifier (found substantially totally in the upper layer) to improve the separation of particles and layers on standing; Examples of such thickeners include hydrophobically modified polyethylene glycols, such as PEG (160) sorbitan triisostearate (ex. Kao) or polyol alkoxy ester and laureth 3 (ex Croda);
 (d) less than about 30%, preferably less than 25% of the total non-chelating electrolyte present in the composition (most is in lower layer) such as, for example, salts of sulphate, bisulphate or a carbonate etc. (e.g., magnesium sulphate); and (2) a lower aqueous layer comprising:
(a) less than 10%, preferably less than 5% of the total surfactant present in the composition of lathering surfactant (greater than 90% and preferably substantially all being found in the upper aqueous layer) as defined in (1)(a) above
(b) less than 25%, preferably less than 20% of total polyalkylene glycol present in the composition (75% or greater of total polyalkylene glycol being found in upper layer) as in (1)(b) above;
(c) less than 15%, preferably less than 10% of total thickener present in the composition (greater than 85% and preferably substantially all being found in upper layer) as defined in (1)(c) above; and
(d) greater than 75%, preferably greater than 85% of the non chelating electrolyte present in the composition as defined in (1)(d) above;

In an unmixed state, the compositions of the invention will separate into two (or more) stable layers. The upper aqueous layer will comprise (a) surfactant; (b) polyalkylene glycol, and/or polyether to improve mildness and separation; (c) thickener to improve separation at standing; (d) electrolyte (non-chelating); and (e) water. The lower layer will have approximately the same ingredients, but the distribution (i.e., % of total component in upper or lower layer) will be different. It is important to emphasize that at least two of the distinct phases are aqueous solutions and that the composition can be prepared without any oil if desired.

More particularly, the upper layer and the lower layer may be anywhere, respectively, from about an 80:20 ratio to about a 20:80 ratio, preferably 70:30 to 30:70, more preferably 60:40 to 40:60. It should be noted that ratios are not exact and are dependent on composition.

Further, the breakdown of components into upper and lower layers can be approximated as follows:

|  | Upper Layer | Lower Layer |
| --- | --- | --- |
| Surfactant | 80% or greater, preferably substantially all | 20% or lower, preferably substantially absent |
| Polyalkylene Glycol | 65% or greater, preferably 70% or greater | 35% or lower, preferably 30% or lower |
| Thickener | 80% or higher, preferably 85% or higher | 20% or lower, preferably 15% or lower, preferably substantially absent |
| Electrolyte | Less than 25%, preferably less than 20% | Greater than 75%, preferably greater than 80% |

The high molecular weight polymers of the invention typically will be found in the upper surfactant rich layer and, as noted, will comprise about 0.1 to less than 1% by wt. of the composition. While not wishing to be bound by theory, it is believed that most of the polymer phase separates in the upper layer. This is believed true because measurements have shown viscosity of lower layer to remain low. Upon mixing, however, the polymers do raise viscosity of the final, mixed composition The components are described in more detail below:

The surfactant generally will comprise 5–35% by wt. of the total composition or 10 to 75% by wt. of the upper aqueous layer. Although it is preferred that greater than 90%, preferably greater than 95% and more preferably substantially all surfactant be present in the upper aqueous layer, as noted, some small amount (less than 20%) may be found in the lower aqueous layer.

The surfactant is a surfactant which may be selected from the group consisting of anionic surfactants, nonionic surfactants, amphoteric/zwitterionic surfactants, cationic surfactants and mixtures thereof. Preferably, there will be at least one anionic surfactant.

Non-limiting examples of anionic surfactants are disclosed in McCutcheon's Detergents and Emulsifiers, North American Edition (1986), published by Allured Publishing Corporation; McCutcheon's Functional materials, North Americas Edition (1992), both of which are incorporated by reference into the subject application.

Examples of anionic surfactants include sarcosinates, sulfates, isethionates, taurates, phosphates, lactylates, glutamates and mixtures thereof. Among isethionates are preferred alkoyl isethionates such as sodium cocoyl isethionate, sodium lauroyl isethionate and mixtures.

The alkyl and alkyl ether sulfates typically have the respective formulae $ROSO_3M$ and $RO(C_2H_4O)_xSO_3M$, wherein R is alkyl or alkenyl of from about 10 to about 30 carbon atoms, x is from about 1 to about 10, and M is a water-soluble cation such as ammonium, sodium, potassium, magnesium and triethanolamine. Another suitable class of anionic surfactants are the water-soluble salts of the organic, sulfuric acid reaction products of the general formula:

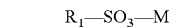

$$R_1\text{—}SO_3\text{—}M$$

wherein $R_1$ is chosen form the group consisting of a straight or branched chain, saturated aliphatic hydrocarbon of radical having from about 8 to about 24, preferably about 10 to about 16, carbon atoms; and M is a cation. Still other anionic synthetic surfactants include the class designated as succinamates, olefin sulfonates having about 12 to about 24 carbon atoms, and $\epsilon_T$-alkyloxy alkane sulfonates. Examples of these materials are sodium lauryl sulfate and ammonium lauryl sulfate.

Other anionic materials useful herein are soaps (i.e., alkali metal salts, e.g., sodium or potassium salts or ammonium or triethanolamine salts) of fatty acids, typically having from about 8 to about 24 carbon atoms, preferably from about 10 to about 20 carbon atoms. The fatty acids used in making the soaps can be obtained from natural sources such as, for instance, plant or animal-derived glycerides (e.g., palm oil, coconut oil, soybean oil, castor oil, tallow, lard, etc.). The fatty acids can also be synthetically prepared. Soaps are described in more detail in U.S. Pat. No. 4,557,853.

Other useful anionic materials include phosphates such as monoalkyl, dialkyl, and trialkylphosphate salts.

Other anionic materials include alkanoyl sarcosinates corresponding to the formula $RCON(CH_3)CH_2CH_2CO_2M$ wherein R is alkyl or alkenyl of about 10 to about 20 carbon atoms, and M is a water-soluble cation such as ammonium, sodium, potassium and alkanolamine (e.g., triethanolamine), a preferred examples of which are sodium lauroyl sarcosinate, sodium cocoyl sarcosinate, ammonium lauroyl sarcosinate, and sodium myristoyl sarcosinate. TEA salts of sarcosinates are also useful.

Also useful are taurates which are based on taurine, which is also known as 2-aminoethanesulfonic acid. Especially useful are taurates having carbon chains between $C_8$ and $C_{16}$. Examples of taurates include N-alkyltaurines such as the one prepared by reacting dodecylamine with sodium isethionate according to the teaching of U.S. Pat. No. 2,658,072 which is incorporated herein by reference in its entirety. Further non-limiting examples include ammonium, sodium, potassium and alkanolamine (e.g., triethanolamine) salts of lauroyl methyl taurate, myristoyl methyl taurate, and cocoyl methyl taurate.

Also useful are lactylates, especially those having carbon chains between $C_8$ and $C_{16}$. Non-limiting examples of lactylates include ammonium, sodium, potassium and alkanolamine (e.g., triethanolamine) salts of lauroyl lactylate, cocoyl lactylate, lauroyl lactylate, and caproyl lactylate.

Also useful herein as anionic surfactants are alkylamino carboxylates such as glutamates, especially those having carbon chains between $C_8$ and $C_{16}$. Non-limiting examples of glutamates include ammonium, sodium, potassium and alkanolamine (e.g., triethanolamine) salts of lauroyl glutamate, myristoyl glutamate, and cocoyl glutamate.

Non-limiting examples of preferred anionic lathering surfactants useful herein include those selected from the group consisting of sodium lauryl sulfate, ammonium lauryl sulfate, ammonium laureth sulfate, sodium laureth sulfate, sodium trideceth sulfate, ammonium cetyl sulfate, sodium cetyl sulfate, ammonium cocoyl isethionate, sodium lauroyl isethionate, sodium lauroyl lactylate, triethanolamine lauroyl lactylate, sodium caproyl lactylate, sodium lauroyl sarcosinate, sodium myristoyl sarcosinate, sodium cocoyl sarcosinate, sodium lauroyl methyl taurate, sodium cocoyl methyl taurate, sodium lauroyl glutamate, sodium myristoyl glutamate, and sodium cocoyl glutamate and mixtures therefor.

Especially preferred for use herein is ammonium lauryl sulfate, ammonium lauryl ether sulfate, sodium lauryl ether sulfate, sodium lauroyl sarcosinate, sodium cocoyl sarcosinate, sodium myristoyl sarcosinate, sodium lauroyl lactate, and triethanolamine lauroyl lactylates.

Nonionic Lathering Surfactants

Non-limiting examples of nonionic lathering surfactants for use in the compositions of the present invention are disclosed in McCutcheon's, Detergents and Emulsifiers, North American Edition (1986), published by allured Published Corporation; and McCutcheon's, Functional materials, North American Edition (1992); both of which are incorporated by reference herein in their entirety.

Nonionic lathering surfactants useful herein include those selected form the group consisting of alkyl glucosides, alkyl polyglucosides, polyhydroxy fatty acid amides, alkoxylated fatty acid esters, alcohol ethoxylates, lathering sucrose esters, amine oxides, and mixtures thereof.

Alkyl glucosides and alkylipolyglucosides are useful herein, and can be broadly defined as condensation articles of long chain alcohols, e.g., C8–30 alcohols, with sugars or starches or sugar or starch polymers i.e., glycosides or polyglycosides. These compounds can be represented by the formula $(S)_n$—O—R wherein S is a sugar moiety such as glucose, fructose, mannose, and galactose; is an integer of from about 1 to about 1000, and R is a C8–30 alkyl group. Examples of long chain alcohols from which the alkyl group can be derived include decyl alcohol, cetyl alcohol, stearyl alcohol, lauryl alcohol, myristyl alcohol, oleyl alcohol and the like. Preferred examples of these surfactants include those wherein S is a glucose moiety, R is a C8–20 alkyl group, and n is an integer of from about 1 to about 9. Commercially available examples of these surfactants include decyl polyglucoside (available as APG 325 CS from Henkel) and lauryl polyglucoside (available as APG 600 CS and 625 CS from Henkel). Also useful are sucrose ester surfactants such as sucrose cocoate and sucrose laurate.

Other useful nonionic surfactants include polyhydroxy fatty acid amide surfactants, more specific examples of which include glucosamides, corresponding to the structural formula:

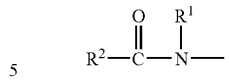

wherein $R^1$ is H, $C_1$–$C_4$ alkyl, 2-hydroxyethyl, 2-hydroxypropyl, preferably $C_1$–$C_4$ alkyl, more preferably mithel or ethyl, most preferably methyl; $R^2$ is $C_5$–$C_{31}$ alkyl or alkenyl, preferably $C_7$–$C_{19}$ alkyl, or alkenyl, more preferably $C_9$–$C_{17}$ alkyl or alkenyl, most preferably $C_{11}$–$C_{15}$ alkyl or alkenyl; and Z is a polyhydroxy hydrocarbyl moiety having a linear hydrocarbyl chain with at least 3 hydroxyl directly connected to the chain, or an alkoxylated derivative (preferably ethoxylated or propyxylated) thereof. Z preferably is a sugar moiety selected from the group consisting of glucose, fructose, maltose, lactose, galactose, mannose, xylose, and mixtures thereof. As especially preferred surfactant corresponding to the above structure is coconut alkyl N-methyl glucoside amide (i.e., wherein the $R^2CO$-moiety is derived form coconut oil fatty acids). Processes for making compositions containing polyhydroxy fatty acid amides are disclosed, for example, in GB Patent Specification 809,060, published Feb. 18, 1959, by Thomas Hedley & Co., Ltd.; U.S. Pat. No. 2,965,576, to E. R. Wilson, issued Dec. 20, 1960; U.S. Pat. No. 2,703,798 to A. M. Schwartz, issued Mar. 8, 1955; and U.S. Pat. No. 1,985,424, to Piggott, issued Dec. 25, 1934; which are incorporated herein by reference in their entirety.

Other examples of nonionic surfactants include amine oxides. Amine oxides correspond to the general formula $R_1R_2R_3NO$, wherein $R_1$ contains an alkyl, alkenyl or monohydroxyl alkyl radical of from about 8 to about 18 carbon atoms, from 0 to about 10 ethylene oxide moieties, and from 0 to about 1 glyceryl moiety, and $R_2$ and $R_3$ contain from about 1 to about 3 carbon atoms and from 0 to about 1 hydroxy group, e.g., methyl, ethyl, propyl, hydroxyethyl, or hydroxypropyl radicals. The arrow in the formula is a conventional representation of a semipolar bond. Examples of amine oxides suitable for use in this invention include dimethyldodecylamine oxide, oleyldi(2-hydroxyethyl) amine oxide, dimethyloctylamine oxide, dimethyl-decylamine oxide, dimethyl-tetradecylamine oxide, 3,6,9-trioxaheptadecyldiethylamine oxide, di(2-hydroxyethyl)-tetradecylamine oxide, 2-dodecoxyethyidimethylamine oxide, 3-dodecoxy-2-hydroxypropyldi(3-hydroxypropyl)amine oxide, diemethylhexadecyclamine oxide.

Non-limiting examples of preferred nonionic surfactants for use herein are those selected form the group consisting of C8–C14 glucose amides, C8–C14 alkyl polyglucosides, sucrose cocoate, sucrose laurate, lauramine oxide, cocoamine oxide, and mixtures thereof.

Amphoteric Lathering Surfactants

The term "amphoteric lathering surfactant," as used herein, is also intended to encompass zwitterionic surfactants, which are well known to formulators skilled in the art as a subset of amphoteric surfactants.

A wide variety of amphoteric lathering surfactants can be used in the compositions of the present invention. Particularly useful are those which are broadly described as derivatives of aliphatic secondary and tertiary amines, preferably wherein the nitrogen is in a cationic state, in which the aliphatic radicals can be straight or branched chain and wherein one of the radicals contains an ionizable water solubilizing group, e.g., carboxy, sulfonate, sulfate, phosphate, or phosphonate.

Non-limiting examples of amphoteric surfactants useful in the compositions of the present invention are disclosed in McCutcheon's, Detergents and Emulsifiers, North American Edition (1986), published by Allured Publishing Corporation; and McCutcheon's, Functional Materials, North American Edition (1992); both of which are incorporated by reference herein in their entirety.

Non-limiting examples of amphoteric or zwitterionic surfactants are those selected from the group consisting of betaines, sultaines, hydroxysultaines, alkyliminoacetates, iminodialkanoates, aminoalkanoates, and mixtures thereof.

Examples of betaines include the higher alkyl betaines, such as coco dimethyl carboxymethyl betaine, lauryl dimethyl carboxymethyl betaine, lauryl dimethyl alphacarboxyethyl betaine, cetyl dimethyl carboxymethyl betaine, cetyl dimethyl betaine (available as Lonaine 16SP from Lonza Corp.), lauryl bis-(2-hydroxyethyl) carboxymethyl betaine, oleyl dimethyl gamma-carboxypropyl betaine, lauryl bis-(hydroxypropyl)alpha-carboxyethyl betaine, coco dimethyl sulfopropyl betaine, lauryl dimethyl sulfoethyl betaine, lauryl bis-(2-hydroxyethyl) sulfopropyl betaine, amidobetaines and amidosulfobetaines (wherein the RCONH(CH$_2$)3 radical is attached to the nitrogen atom of the betaine), oleyl betaine (available as amphoteric Velvetex OLB-50 from Henkel), and cocamidopropyl betaine (available as Velvetex BK-35 and BA-35 from Henkel).

Example of sultaines and hydroxysultaines include materials such as cocamidopropyl hydroxysultaine (available as Miratine CBS from Rhone-Poulenc).

Preferred for use herein are amphoteric surfactants having the following structure:

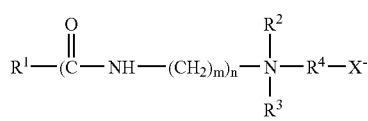

wherein $R^1$ is unsubstituted, saturated or unsaturated, straight or branched chain alkyl having from about 9 to about 22 carbon atoms. Preferred $R^1$ has from about 11 to about 18 carbon atoms; more preferably from about 12 to about 18 carbon atoms; more preferably still from about 14 to about 18 carbon atoms; m is an integer from 1 to about 3, more preferably from about 2 to about 3, and more preferably abort a3; n is either 0 or 1, preferably 1; $R^2$ and $R^3$ are independently selected from the group consisting of alkyl having from 1 to about 3 carbon atoms, unsubstituted or mono-substituted with hydroxy, preferred $R^2$ and $R^3$ are CH$_3$; X is selected form the group consisting of CO$_2$, SO$_3$ and SO$_4$; $R^4$ is selected form the group consisting of saturated or unsaturated, straight or branched chain alkyl, unsubstituted or mono-substituted with hydroxy, having from 1 to about 5 carbon atoms. When X is CO$_2$, $R^4$ preferably has 1 to 3 carbon atoms, more preferably 1 carbon atom. When X is SO$_3$ or SO4, $R^4$ preferably has from about 2 to about 4 carbon atoms, more preferably 3 carbon atoms.

Examples of amphoteric surfactants of the present invention include the following compounds:

Cetyl dimethyl betaine (this material also has the CTFA designation cetyl betaine);

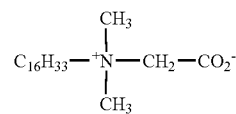

Cocamidopropylbetaine

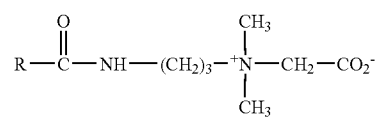

Cocamidopropyl hydroxy sultaine
wherein R has from about 9 to about 13 carbon atoms

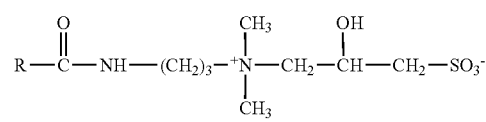

wherein R has from about 9 to about 13 carbon atoms.

Cationic Surfactants

Cationic surfactants are another useful class of surfactants that can be employed as auxiliary agents. They are particularly useful as additives to enhance skin feel, and provide skin conditioning benefits. One class of cationic surfactants is heterocyclic ammonium salts such as cetyl or stearyl pyridinium chloride, alkyl amidoethyl pyrrylinodium methyl sulfate, lapyrium chloride.

Tetra alkyl ammonium salts is another useful class of cationic surfactants. Examples include cetyl or stearyl trimethyl ammonium chloride or bromide; hydrogenated palm or tallow trimethylammonium halides; behenyl trimethyl ammonium halides or methyl sulfates; decyl isononyl dimethyl ammonium halides; ditallow (or distearyl) dimethyl ammonium halides; behenyl dimethy ammonium chloride.

Other types of cationic surfactants that can be employed are the various ethoxylated quaternary amines and ester quats. Examples are PEG-5 stearyl ammonium lactate (e.g., Genamin KSL manufactured by Clarion), PEG-2 coco ammonium chloride, PEG-15 hydrogenated tallow ammonium chloride, PEG 15 stearyl ammonium chloride, dialmitoyl ethyl methyl ammonium chloride, dipalmitoyl hydroxyethyl methyl sulfate, strearyl amidopropyl dimethylamine lactate.

Still other useful cationic surfactants are quaternized hydrolysates of silk, wheat, and keratin proteins.

Polyalkylene Glycol

The polyalkylene glycol generally will comprise 5% to 25% by wt., preferably 7 to 20% by wt. total composition. The polyalkylene glycol will generally divide into at least 65%, preferably 70% of polyalkylene glycol in the upper layer and less than 35%, preferably less than 30% in the lower layer.

Because the compositions of the invention are personal wash compositions primarily intended for contact with skin during wash, the polyalkylene glycol (whose function is to help keep surfactant dissolved in upper aqueous layers, but which may also function as moisturizing benefit agent)

should be an alcohol, glycol or polyether of minimal molecular weight which is not irritating to the skin.

Examples of such include alcohols, particularly polyalkylene oxides having MW 200–6000, preferably 200 to 3000. The polyalkylene glycol can be comprised of ethylene oxide, propylene oxide, butylene oxide or their mixtures either as polymers or copolymers. Specific examples include polyethylene glycols such as PEG 400.

Thickeners

The thickeners of the invention will generally comprise 1 to 12%, preferably 2 to 10% by wt. of composition. In one preferred embodiment of the invention, greater than 80%, preferably greater than 85% and most preferably substantially all of the thickeners/viscosity modifier will be found in the upper aqueous layer although 20% or less, preferably 15% or less, preferably 5% or less may be found in lower layer.

The thickener/viscosity modifier serves to thicken the upper layer and maintain separation upon standing.

Thickeners which may be used include hydrophobically modified polyethers. Examples of this class of thickeners which may be used include but are not limited to sugar esters such as PEG (160) sorbitan triisostearate (Rheodol TWS-399C ex Kao Chemicals) or PEG-120 Pentaerythrityl Tetrastearate ex Croda. Other examples include Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt).

Another class of suitable polymers are hydrophobically modified cellulose ethers including but not limited to hydroxyethyl cellulose, hydroxypropylcellulose and cellulose ethers with long pendant chains such as nonoxynyl hydroxyethylcellulose (Amerchol Polymer HM 1500)

Another class of suitable polymers are the hydrophobically modified acrylate copolymers such as Antil 208® (ex Goldschmidt) (acrylate/steareth-50 acrylate copolymer).

Another class of suitable polymers are the hydrophobically modified polyurethanes such as Acrysol series (e.g., Acrysol RM-2020) from Rhom and Haas.

Another class of suitable thickeners are xanthan gums, guar gums and chemically modified guar gums.

Electrolyte

The compositions of the invention further comprise less than about 30%, preferably less than 25% of an electrolyte. The electrolyte should preferably not be a chelating electrolyte (which are typically poor in biodegradability). Typically, no more than 25%, preferably 15% or less, more preferably 10% or less of the electrolyte should be in the upper layer while 75% or more, preferably 85% or more should be in the lower layer.

Typically, the electrolyte should be a salt of a sulphate, bisulfate, carbonate, bicarbonate, phosphate, etc. Examples include sodium, potassium sulphate and ammonium sulphate. Magnesium sulphate is particularly preferred.

Aqueous solubility of the salt should exceed 30% wt. to volume at 0° C. such that it may be observed that mineral salts will generally be more preferred than organic salts which typically have much lower solubility.

The high molecular weight polymers of the invention are typically polymers which have molecular weight of at least 5,000, preferably at least 10,000, more preferably at least 25,000.

Theoretically, any viscosity enhancing polymer may be used although the polymer(s) chosen must have the ability to both enhance viscosity and ensure that biphasic composition is stably induced. Thus, some classes of viscosity enhancing polymers may be better than others at maximizing viscosity increase.

Among preferred classes of viscosity enhancing copolymer or polymers which will not interfere with successful biphasic inducing, for example, are (1) non-starch polysaccharides such as cellulose polymers and derivatives of such including, for example, methyl cellulose, ethyl cellulose, carboxymethyl cellulose (CMC), hydroxyethyl cellulose (HEC), hydrophobically modified HEC (HMHEC), methyl hydroxyethyl or methyl hydroxypropyl cellulose (MHEC or MHPC), ethylhydroxyethyl cellulose (EHEC) and mixtures of the above; (2) high molecular weight, starch based polysaccharides, especially water soluble (e.g., dissolve at least 10% by wt. in water) polysaccharides; (3) polyvinylpyrrolidone polymers of MW 5,000 to 300,000, preferably 10,000 to 150,000; (4) polyvinyl alcohol polymers; (5) vinyl acetate polymers; and (6) copolymers of the above (e.g., polyvinylpyrollidone—vinyl acetate copolymers), and/or mixtures of the above.

As noted, non-starch polysaccharides may include any of the cellulose polymers, for example, indicated above.

High molecular weight, starch-based polymers are also useful for enhancing viscosity.

Especially preferred are water soluble, preferably highly water soluble (e.g., dissolve at level of at least about 10% by weight in water) polysaccharides. Preferably these form stable solutions at ambient temperature and preferably the polysaccharides also form clear isotropic solutions in water at room temperature.

Without wishing to be bound by theory, suitable starch based polysaccharides tend to be nonionic in character, and tend to have a molecular structure that inhibits molecular association especially in water, e.g., branching, kinks or small pendant groups appearing with sufficiently high frequency, i.e., short repeat lengths.

Many such polysaccharides are described in the treatise edited by R. L. Whistler and J. N. BeMiller, "Industrial Gums: Polysaccharides and Their Derivatives", $3^{rd}$ Edition, Academic Press Inc., San Diego, Calif. (1993), herein after called "Whistler" and incorporated by reference herein in its entirely.

One suitable class of polymers is pullulan which is described in Whistler, Chapter 16, p 447. Pullulan is a class of glucans elaborated extra cellularly by the fungus *Aureobasidium* (also known as *Pullularia*). Pullulan dissolves readily in water to form stable viscous solutions that do not gel.

The structure of Pullulan is reported to be predominantly based maltotriose units jointed by alpha (1–6) linkages.

Depending upon the strain of fungus employed, the molecular weight of pullulan can vary between 1,000 to 3,000,000 daltons. However, for the purposes of the present application, the molecular weight should be greater than about 10,000, preferably greater than 50,000 and most preferably between 100,000 and 300,000 daltons. Pullulan is available from Hayashibara and sold under the trade name Pullulan PI-20. A particular pullulan from Hayashibara having an average molecular weight of 200,000 was suitable.

Another class of viscosity enhancing molecules which may be used are those with a ring structure, preferably 5 or 6 member ring structure wherein the ring structure is chemically bonded to a polymerizable vinyl group to form a vinyl polymer (e.g., with pendant ring structure). The molecules have MW 5000 to 500,000, preferably 10,000 to 250,000.

The molecules may include vinyl benzene (e.g., styrene) or derivatives of vinyl benzene or molecules where the ring contains an atom such as nitrogen (e.g., pyrrole and pyrrole derivatives), oxygen (e.g., furan and furan derivatives) or sulfur (e.g., thiophene and thiophene derivatives) which are chemically attached to the polymerizable vinyl group to form the vinyl polymer.

One preferred class are polyvinylpyrrolidones of varying molecular weight, e.g., 5000 to 250,000.

Another class of molecules are the polyvinyl alcohol polymers wherein, for example, OH is chemically bonded to polymerizable vinyl group to form polyvinyl alcohol polymer. Again, molecular weight of polymer is typically from about 5000 to 250,000.

Yet another class of molecule are molecules in which $C_1$–$C_6$ carboxylic acid group (e.g., acetic acid) is chemically to polymerizable vinyl group to form polymer (e.g., vinyl acetate).

The viscosity enhancing polymer may comprise a copolymer which may be a copolymer of any of the groups described above which are, for example, block polymerized. One example of this are polyvinylpyrrolidone/vinyl acetate copolymer such as shown below, for example:

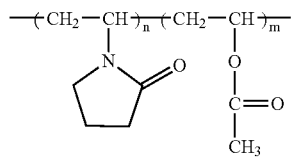

wherein values of n and m are such that polymer has MW of 20,000 to 250,000.

By chemically bonded (or attached) is meant that there is a bond between an atom on the polymer (e.g., OH group on the alcohol) and, for example, a carbon atom on the vinyl backbone chain.

The polymer may also be a mixture of any of the molecules (polymer and/or copolymers) noted above.

In a second preferred embodiment, the invention relates to aqueous/aqueous biphasic liquids, formed using polydextrose as biphasic inducing agent.

More specifically, the invention comprises:
(1) 5% to 75% by wt. of a surfactant selected from the group consisting of anionic surfactant, nonionic surfactants, amphoteric/zwitterionic, cationic surfactant and mixtures thereof;
(2) at least 15% polydextrose, wherein the degree of polymerization (i.e., number of linking glucose units) is 4 to 22 or have an MW of 600 to 3600; preferably MW is 700 to 1800, more preferably 900 to 1500 and more preferably 900 to 1200;
(3) balance water and minors; and
(4) 0.1 to less than 1% high MW polymer.

The compositions may be used in combination with a transparent package in order to view the liquid. Thus, a system comprising said transparent or translucent package in combination with the liquid compositions is also contemplated.

In a second aspect of this embodiment of the invention, a small amount of salt is used and the amount of polydextrose needed to induce biphasic liquid is reduced. More specifically, in this embodiment, the composition comprises at least 1% salt and at least 10% polydextrose.

The compositions may comprise at least 2% salt and at least 5% polydextrose.

The surfactant used may be any of the surfactants discussed in connection with the first biphasic embodiment of the invention.

The compound which is added to the formulation which induces formation of biphasic (multiphasic) liquid is polydextrose. Generally, the polydextrose has a formulation as follows:

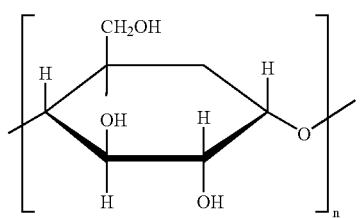

wherein n (defining number of linking glucose units) is from about 4 to about 22.

The biphasic inducing polydextrose compounds of the invention may also be defined by molecular weight in that they should have MW range of from 600 to about 3600, more preferably 700 to 3000, more preferably 700 to 1800, more preferably 900 to 1500.

Whether defined by glucose units or MW, it should be understood that the critical point is that the structure is such as to induce formation of a multiphasic/biphasic formulation defined by those characteristics which in turn define the biphasic liquid (e.g., viscosity of and stability in the biphasic state).

The amount of polydextrose used to induce biphasic state may vary depending on whether salt/electrolyte is used.

Thus, for example, if no salt is used (use of no or little salt also distinguishes this invention from other biphasic liquids of the art where relatively large amounts of salt, e.g., greater than 3% by wt., are in fact required to induce the biphasic liquid), then there is needed at least 15% by wt. of polydextrose to induce biphasic separation. If some salt is added (e.g., at least 0.5%, preferably at least 1.0%), the amount of polydextrose needed goes down to 10% by wt. If at least 2% salt is used, the amount of polydextrose may be 5%.

There is also generally a balance between amount of surfactant used and amount of polydextrose. Generally lower surfactant requires more polydextrose and, conversely, more surfactant requires less polydextrose. Thus, for example, 5% to 10% by wt. surfactant may require about 40% or more polydextrose and 35% surfactant may need only about 10–15% polydextrose, even in the absence of salt.

Generally, the upper limit of polydextrose used is about 75%. This is not an upper limit with regard to inducing biphasic liquid.

If electrolyte/salt is used, it typically will be used in amount of 0.5% to no higher than 4%, preferably no higher than about 3% by wt. of total composition.

Preferably, the electrolyte is not a chelating electrolyte (these are generally poor in biodegradability).

Typically, the electrolyte should be a salt of a sulphate, bisulfate, carbonate, bicarbonate, phosphate, chloride, etc. Examples include sodium sulphate, potassium sulphate, ammonium sulphate, sodium chloride, and magnesium chloride. Magnesium sulphate and sodium chloride are particularly preferred.

The high molecular weight polymers may be any of those described in connection with the first embodiment biphasic liquid above (e.g., non-starch polysaccharides, high molecular weight starch based polysaccharides etc.)

Finally, the balance of composition is water and minors.

Optional

The following optional ingredients may be used in the multiphasic/biphasic compositions of the invention.

The composition may contain polyalkylene glycol. The polyalkylene glycol should be an alcohol, glycol or polyether of minimal molecular weight which is not irritating to the skin.

Examples of such include alcohols, particularly polyalkylene oxides having MW 200–6000, preferably 200 to 3000. The polyalkylene glycol can be comprised of ethylene oxide, propylene oxide, butylene oxide or their mixtures either as polymers or copolymers. Specific examples include polyethylene glycols such as PEG 400. As noted, use of such alcohols is not required.

The composition may further comprise thickeners. Generally, the thickener/viscosity modifier serves to thicken the upper and/or lower layer.

Thickeners which may be used include hydrophobically modified polyethers. Examples of this class of thickeners which may be used include but are not limited to sugar esters such as PEG (160) sorbitan triisostearate (Rheodol TWS-399C ex Kao Chemicals) or PEG-120 Pentaerythrityl Tetrastearate ex Croda. Other examples include Glucam DOE 120 (PEG 120 Methyl Glucose Dioleate); Rewoderm® (PEG modified glyceryl cocoate, palmate or tallowate) from Rewo Chemicals; Antil® 141 (from Goldschmidt); and Carbopol® polymers from Noveon.

Another class of suitable polymers are hydrophobically modified cellulose ethers including but not limited to hydroxyethyl cellulose, hydroxypropylcellulose and cellulose ethers with long pendant chains such as nonoxynyl hydroxyethylcellulose (Amerchol Polymer HM 1500).

Another class of suitable polymers are the hydrophobically modified acrylate copolymers such as Antil 208® (ex Goldschmidt) (acrylate/steareth-50 acrylate copolymer).

Another class of suitable polymers are the hydrophobically modified polyurethanes such as Acrysol series (e.g., Acrysol RM-2020) from Rhom and Haas.

Another class of suitable thickeners are xanthan gums, guar gums and chemically modified guar gums.

In addition to the ingredients noted above, the compositions of the invention may contain hydrotropes including but not limited to short chain monohydric or dihydric alcohols, xylene sulphonate and hexylene glycol whose purpose is to avoid the formation of liquid crystal phases resulting from the separation of the surfactant material into the upper phase hence increasing its apparent concentration.

The compositions may comprise benefit agents. Benefit agent may be any material that has potential to provide an effect on, for example, the skin.

The benefit agent may be water insoluble material that can protect, moisturize or condition the skin upon deposition from compositions of invention. These may include silicon oils and gums, fats and oils, waxes, hydrocarbons (e.g., petrolatum), higher fatty acids and esters, vitamins, sunscreens. They may include any of the agents, for example, mentioned at column 8, line 31 to column 9, line 13 of U.S. Pat. No. 5,759,969, hereby incorporated by reference into the subject application.

The benefit agent may also be a water soluble material such as glycerin, polyols (e.g., saccharides), enzyme and α- or β-hydroxy acid either alone or entrapped in an oily benefit agent.

The benefit agent may be found in either the upper or the lower layer depending on its solubility and partition coefficient, for example, oil may partition into the upper layer while more water soluble agents (e.g., alpha hydroxy acids) may go into the lower.

The compositions may comprise perfumes, sequestering agents such as EDTA EHDP in amounts 0.01 to 1%, preferably 0.01 to 0.05%; coloring agents, opacifiers and pearlizers such as zinc stearate, magnesium stearate, TiO2, mica, EGMS (ethylene glycol monostrearate) or styrene/acrylate copolymers.

The compositions may further comprise antimicrobials such as 2-hydroxy 4,2'4' trichlorodiphenylether (DP300), 3,4,4'-trichlorocarbanilide, essential oils and preservatives such as dimethyl hydantoin (Glydant XL 1000), parabens, sorbic acid etc.

The compositions may also comprise coconut acyl mono or diethanol amides as suds boosters, and strongly ionizing salts such as sodium chloride and sodium sulfate may also be used to advantage.

Antioxidants such as, for example, butylated hydroxytoluene (BHT) may be used advantageously in amounts of about 0.01% or higher if appropriate.

Cationic conditioners which may be used including Quatrisoft LM-200 Polyquaternium-24, Merquat Plus 3330-Polyquaternium 39; and Jaguar® type conditioners.

Composition may also include clays such as Bentonite® claims as well as particulates such as abrasives, glitter, and shimmer.

The minors and optional noted above can also be used in connection with there first embodiment biphasic of the invention.

Finally, in a third embodiment of the invention, the invention comprises a process for enhancing viscosity of the biphasic liquid which process comprises ensuring the high molecular weight polymers noted above are used in the formation of biphasic liquids. The polymers are added in an amount of from 0.1 to less than 1% by wt. of the composition.

Methodology

Measurement of Viscosity

Description

Haake Rheometer was used to measure the viscosities of liquid and semisolid personal wash products in the small scale with the viscosity measured at various shear rates.

Equipment

The instrument was an RV 20 Rotovisco RC 20 rheometer which includes a stand and sample temperature control unit, cups and bobs for loading the sample, a waterbath which is maintained at 25° C. and a computer and plotter to manipulate and record the data.

Operational Procedure

Haake rheometer, computer, monitor and printer were turned on.

Water bath: Waterbath was filled with water to a required level, the appropriate temperature was set and water bath was turned on.

Measurement Systems: Sample was loaded into rheometer and equilibrated to 25° C.

a) the appropriate cup and bob for the product are selected as noted below.
   i) NV for viscosity measurements of low viscous products, e.g. diluted solutions, fruit juices, etc;
   ii) SV1 for viscosity measurements of high viscosity liquids working in the low to medium range which consists of a SV cup with a rotor(bob). This is the cup and bob that is typically used to measure shower gel products;
b) the rotor(bob) was secured on to the top segment of the measuring system;
c) the RV 20 rheometer was adjusted using the zero button;
d) sample was poured into the cup until almost three fourths filled (approx. 20 g) and then the cup was carefully slid through the temperature controller and screwed to the main segment of the rheometer so that it was immersed in the product and sample was slightly above the rim of the bob;
e) waited 5 to 10 minutes after loading the sample to ensure equilibration of sample to set temperature (set parameters on computer while waiting for temperature equilibration).

Computer:
a) floppy disc was inserted and previous standard file was loaded if one is already saved on disc. If not, the following details were loaded into the computer:
   i) measurement: select SV1, NV1, SV2P depending on the spindle used;
   ii) select four segments for four shear rates, 1, 10, 100, 400 at 25° C. and in 10 steps;
b) on the computer screen follow the steps below to load the above details: measurement—identification (record details of the sample); measurement—parameter—select SV1; measurement—go immediately (after sample is equilibrated);
c) this starts the measurement which takes about 10 minutes;
d) once the measurement was completed, results were saved on floppy disk; results were either printed or set as graphical representation.

Results

The results were recorded as viscosity in mPas (cps) at the shear rates: 1/sec, 10/sec and 100/sec. The temperature and spindle (bob) size were recorded with each sample measurement.

EXAMPLES

Example 1

Preparation of Polydextrose Glycol/Salt Biphasic for Typical Formulations

In the case of biphasic liquids induced by polyalkylene glycol and salt, the composition is prepared in batch process as follows:

Polyalkylene glycol (e.g., polyethylene glycol) and surfactant (sodium lauryl ether (2EO) sulphate) are premixed. Water is slowly added with continuous mixing while heating to about 70° C. High molecular weight polymer is added. Thickener (e.g., polyethylene glycol (50) sorbitan triisostearate) is added and mixed to homogeneous. Electrolyte (e.g., magnesium sulphate heptahydrate) is added. Mixture is allowed to cool to about 40° C. before adding perfume and other ingredients. Constant mixing is used to prevent premature phase separation before filling. A typical composition as noted below is made.

| Ingredient | % w/w |
|---|---|
| Sodium lauryl Ether (2 EO) Sulphate | 19.00 |
| Polyethylene Glycol Av. Mwt. 400 | 11.00 |
| Polyethylene Glycol (160) Sorbitan Triisostearate | 4.00 |
| Magnesium Sulphate (hydrated)* | 17.4 |
| Sodium Chloride | 0.25 |
| Perfume | 0.50 |
| Preservative | 0.05 |
| Dye | 0.0002 |
| Distilled Water | 47.8 |

*May be anhydrous, but would lower level of salt and increase level of water.

Example 2

Preparation

A typical example of the invention was made as follows:

Maltodextrin was first slowly dissolved in water. Surfactants (i.e., commercial blend comprising laureth sulfate, lauryl sulfate, cocomonoethanolamide and ethanolamine) were added and composition was heated to above 50° C. The viscosity building polymers were added and mixed to homogeneous and electrolyte (e.g., magnesium sulfate) as well as minors (except perfumes and minors added later) were added. The mixture was allowed to cool to about 35° C. before adding ingredients. Constant mixing was used to prevent premature phase separation before filling.

The following typical compositions were prepared and the specific high MW polymers used are identified in examples to follow:

| Ingredient | % by wt. |
|---|---|
| Ammonium laureth (1 EO) sulfate | 4.6 |
| Ammonium lauryl sulfate | 6.1 |
| Cocomonoethanolamide | 1.0 |
| PEG-5 Cocomonoethanolamide | .5 |
| High MW Polymer (e.g., PVP/VA) | 0.1–1% |
| MgSO$_4$ | 3 |
| Maltodextrin | 20 |
| Glycerin | 0.5 |
| Perfume, colorant, preservatives | 1.5 |
| Water | To 100% |

Examples 3 to 11 & Comparatives

Using the process of Example 2, the following compositions were prepared.

| Ingredients | Comp A | Ex 3 | Ex 4 | Ex 5 | Ex 6 | Ex 7 | Ex 8 | Ex 9 | Ex 10 | Ex 11 |
|---|---|---|---|---|---|---|---|---|---|---|
| Surfactant (Blend) | 14% | 14% | 14% | 14% | 14% | 14% | 14% | 14% | 14% | 14% |
| Polymer or other added | | .5% hydroxy Ethyl cellulose | .5% Pullulan | 0.4% PVAL | 0.8% PVAL | .5% PVP K30 | .5% PVP K90 | .5% PVP K120 | 1% PVP/VA W-735 | .25 PVP/VA-735 |
| Maltodextrin | 20% | 20% | 20% | 20% | 20% | 20% | 20% | 20% | 20% | 20% |
| MgSO$_4$ | 3% | 3% | 3% | 3% | 3% | 3% | 3% | 3% | 3% | 3% |
| Glycerin | 0.5% | | 0.5% | 0.5% | 0.5% | 0.5% | 0.5% | 0.5% | 0.5% | 0.5% |
| Perfume & Minors | 0.8% | .85% | .85% | .85% | .85% | .85% | .85% | .85% | .85% | .85% |
| Water | To 100% | To 100% | To 100% | 100% | To 100% | To 100% | To 100% | To 100% | To 100% | To 100% |
| Viscosity at 10$^{-1}$ (10 shakes) | 82 | 320 | 266 | 305 | 550.9 | 234 | 209 | 143 | 309.0 | 260 |

Surfactant blend was mixture of ammonium laureth sulfate, ammonium lauryl sulfate, cocomonoethanolamide and PEG-5 cocomonoethanolamide.
PVP is polyvinylpyrollidone
PVAL is polyvinylalcohol
PVP/VA W735 is a copolymer of PVP and vinylacetate (70% PVP 30 VA in water) supplied by ISP From the Table/Examples above, several things may be noted. First, where no high molecular weight polymer was used in the composition (See Comparative A), viscosity after shaking is only 82 mPas (using SV1 spindle/cap at shear rate of 10S$^{-1}$. As seen, when using 0.1 to 1% of the high molecular weight polymers of the invention resulted in substantial increase in viscosity without affecting ability of phases to mix and subsequently separate.

The invention claimed is:

1. A biphasic liquid product composition comprising:
   (a) 5 to 50% of a surfactant selected from the group consisting of anionic surfactants, nonionic surfactants, amphoteric/zwitterionic surfactants, cationic surfactants and mixtures thereof;
   (b) at least about 15% of a polydextrose molecule or molecules, wherein the degree of polymerization is about 4 to 22 (corresponding to MW about 600 to about 3600);
   (c) balance water and minors,
      wherein said composition comprises at least two visibly separated aqueous based layers when left sitting without shaking or stirring; and
   (d) 0.01 to less than 1% by wt. of polymer and/or copolymer having molecular weight of at least 10,000, wherein said polymer enhances viscosity at least 5% relative to same composition without polymer.

2. A composition according to claim 1, wherein polymer enhances viscosity at least 10% relative to same composition without polymer.

3. A composition according to claim 2, wherein polymer enhances viscosity at least 20%.

4. A composition according to claim 1, wherein polymer and/or copolymer has molecular weight of 10,000 to 500,000.

5. A composition according to claim 1 wherein said viscosity enhancing polymer is selected from the group consisting of non-starch polysaccharides; starch-based, water-soluble polysaccharides; molecules with a ring structure, wherein said ring structure is chemically bonded to a polymerizable vinyl group to form a vinyl polymer; polyvinyl alcohol wherein alcohol group is chemically bonded to polymerizable vinyl group to form polyvinyl alcohol polymer; molecule with C$_1$ to C$_6$ carboxylic acid group chemically bonded to polymerizable vinyl group to form vinyl polymer; copolymer which is a mixture of groups described above; and mixture of the above groups.

6. A composition according to claim 5, wherein the non-starch polysaccharide comprises cellulose polymers and derivatives thereof.

7. A composition according to claim 5, wherein said starch based water soluble polysaccharide dissolves at a level of at least about 10% in water.

8. A composition according to claim 7, wherein said polysaccharide is pullulan.

9. A composition according to claim 5, wherein the molecule with a ring structure has a 5 or 6 member ring structure and the vinyl polymer formed has MW of 10,000 to 500,000.

10. A composition according to claim 9, wherein said molecule is selected from the group consisting of benzene and derivatives of benzene; molecules where ring contains at least one nitrogen chemically bonded to polymerizable vinyl group; molecules where ring group contains at least one oxygen chemically bonded to polymerizable vinyl group; and molecules where ring contains at least one sulfur chemically bonded to polymerizable vinyl group.

11. A composition according to claim 10, wherein molecule with at least one nitrogen in ring group is polyvinylpyrrolidone.

12. A composition according to claim 5 wherein molecule with C$_1$ to C$_6$ carboxylic group is vinyl acetate.

13. A composition according to claim 12 wherein copolymer which is a mixture of at least two groups comprises a block copolymer of polyvinylpyrrolidone and vinyl acetate.

14. A biphasic liquid personal product composition comprising:
   (a) 5 to 50% by wt. of a surfactant selected from the group consisting of anionic surfactants, nonionic surfactants, amphoteric/zwitterionic surfactants, cationic surfactants and mixtures thereof;
   (b) 1 to 12% by wt. thickener;
   (c) 4 to 20% by wt. polyalkylene glycol;
   (d) a non-chelating mineral salt selected from alkali metal or alkaline earth sulfates, bisulfates, carbonates, bicarbonates, and mixtures thereof, wherein the non-chelating mineral salt is present in an amount sufficient to induce a separation of the aqueous composition into at least two distinct aqueous layers that are present in a volume ratio of upper to lower phase of from 4:1 to 1:4;

wherein on standing the personal product composition forms two or more visibly distinct aqueous phases and, when agitated, the composition forms a visible single phase product, wherein, when left to stand after the composition has been agitated and has formed a single phase, the composition will again form two or more visibly distinct aqueous phases within 24 hours;

(e) 0.01 to less than 1% by wt. of polymer and/or copolymer having molecular weight of at least 10,000, wherein said polymer enhances viscosity at least about 5% relative to same composition without polymer.

15. A process for enhancing viscosity of aqueous/aqueous biphasic liquid compositions comprising components (a), (b) and (c) of claim 1, said process comprising adding 0.01 to less than 1% by wt. of a polymer and/or copolymer having a molecular weight of at least 10,000.

* * * * *